United States Patent [19]
Kridl et al.

[11] Patent Number: 5,110,728
[45] Date of Patent: May 5, 1992

[54] ACYL CARRIER PROTEIN - DNA SEQUENCE AND SYNTHESIS

[75] Inventors: Jean C. Kridl; Vic C. Knauf, both of Davis, Calif.

[73] Assignee: Calgene, Inc., Davis, Calif.

[21] Appl. No.: 437,764

[22] Filed: Nov. 15, 1989

Related U.S. Application Data

[63] Continuation of Ser. No. 78,924, Jul. 28, 1987, abandoned, which is a continuation-in-part of Ser. No. 891,529, Jul. 31, 1986, abandoned.

[51] Int. Cl.$^5$ .................. C12P 21/00; C12P 21/04; C12N 15/00; C12N 5/00; C07H 15/12
[52] U.S. Cl. .................. 435/69.1; 435/69.8; 435/70.1; 435/172.3; 435/240.4; 435/320.1; 536/27; 935/11; 935/30; 935/35; 935/48; 935/67
[58] Field of Search ............ 435/69.1, 69.8, 70.1, 435/172.3, 240.4, 320, 320.1; 536/27; 935/11, 30, 35, 48, 67

[56] References Cited

U.S. PATENT DOCUMENTS 4,888,282  12/1989  Beremand et al. ............... 435/193

FOREIGN PATENT DOCUMENTS 0189707  1/1985  European Pat. Off. .
0255378  2/1988  European Pat. Off. .

OTHER PUBLICATIONS

Willmitzer, "The Use of Transgenic Plants to Study Plant Gene Expression", *Trends in Genetics* (1988) 4:13–18.
Hansen, "Three cDNA Clones for Barley Leaf Acyl Carrier Proteins I and III", *Carlsberg Res. Commun.* (1987) 52:381–392.
Okamuro, et al., "Regulation of Plant Gene Expression: General Principles", *The Biochemistry of Plants* (1989) 15:1–82.
Ohlrogge et al., "Spinach Acyl-Carrier Proteins: Structure, Regulation, and Progress Towards Cloning", *Biochemical Society Transactions* (1986) 14:579–581.
Slabas et al., "Oil Seed Rape Acyl Carrier Protein (ACP) Protein and Gene Structure", *Seventh International Symposium on Plant Lipids*, held Jul. 27–Aug. 1, 1986 (poster presentation).
Crouch et al., *Journal of Molecular and Applied Genetics* (1983) 2:273–283.
Maniatis et al., *Molecular Cloning, A Laboratory Manual*, Second Edition (1989) Cold Spring Harbor Laboratory Press, pp. 10.38–10.43.
Cronan and Rick, "*Escherichia coli* and *Salmonella typhimurium*", *Cellular Molecular Biology*, vol. 1 (1987) American Society for Microbiology, pp. 474–497.
Beremand et al., "Synthesis, Cloning and Expression in *Escherichia coli* of a Spinach Acyl Carrier Protein-I Gene", *Arch. Biochem. Biophys.* (1987) 256:90–100.
Ting, *Plant Physiology* (1982) p. 14.
Boyle et al., "Uptake and Processing of the Precursor to the Small Subunit of Ribulose 1,5-Bisphosphate Carboxylase by Luceoplasts from the Endosperm of Developing Castor Oil Seeds", *Plant Physiol.* (1986) 81:817–822.
Prescott et al., "Acyl Carrier Protein", *Advances in Enzymology* (1972) 36:269–309.
Tsung et al., "A Novel, General Radioimmunoassay for Acyl Carrier Proteins", *Analytical Biochemistry* (1984) 136:497–502.
Ohlrogge, et al., "Spinach Acyl-Carrier Proteins: Structure, Regulation, and Progress Towards Cloning," *Chemical Abstructs* (1986) 105:164, #55584k.
Schmid et al., 1990, Plant Mol. Biol., 15:765–778.
Ohlrogge et al., 1985, J. Biol. Chem. 260(13):8032–8037.
Kuo et al., 1984, Arch. Biochem. Biophys. 234(1):290–296.
Sengupta-Gopalan et al., 1985, Proc. Natl. Acad. Sci.: USA 82:3320–3324.
Van den Broeck et al., 1985, Nature 313:358–363.
Facciotti et al., 1985, Biotechnology 3:241–246.
Fishbein, G. 1986, Genet. Eng. Lett. 6(6):1–4.
Goodman et al., 1987, Science 236:48–54.

*Primary Examiner*—David T. Fox
*Attorney, Agent, or Firm*—Donna E. Scherer

[57] ABSTRACT

DNA sequences are provided coding for acyl carrier protein, which sequence can be used for production of acyl carrier protein as an end product or in plant seed to enhance seed oil production. A regulated promoter is provided which substantially limits expression of the acyl carrier protein to seed tissue.

29 Claims, No Drawings

5,110,728

ACYL CARRIER PROTEIN - DNA SEQUENCE AND SYNTHESIS

This is a continuation of application Ser. No. 078,924, filed Jul. 28, 1987, now abandoned, which is a continuation-in-part of application Ser. No. 891,529, filed Jul. 31, 1986, now abandoned.

FIELD OF THE INVENTION

Acyl carrier protein is expressed under conditions where the protein may be isolated for in vitro use or the protein is intracellularly translocated to a chloroplast or related organelle for modification of fatty acid production in vivo. Constructs are provided which allow for expression of acyl carrier protein in seed tissue using a seed specific promoter.

BACKGROUND OF THE INVENTION

Plants provide a rich source of a variety of products which find use in foods, as raw materials, and as finished products. Vegetable fatty acids find extensive use for a wide variety of commercial purposes, being used as vegetable oils for cooking, as lubricants, in alkyd resins, as specialty chemicals, and the like. For the most part, the plant fatty acids tend to be of 18 carbon atoms, there usually being only a minor level of fatty acids having fewer than 16 carbon atoms. For many purposes, it would be desirable to have fatty acids in the range of 8 to 14 carbon atoms. There is, therefore, substantial interest in developing methods for producing vegetable oils where there is a substantial proportion of the total fatty acids of 14 carbon atoms or fewer.

To achieve this purpose, it will be necessary to modify the constituent members of the metabolic pathway resulting in the formation of fatty acids and their elongation to higher fatty acids. Toward this purpose, it will be necessary to be able to produce one or more components along the fatty acid metabolic chain which modify the course of the plant metabolism. In addition, there may be significant commercial applications for individual components of the fatty acid metabolic pathway.

BRIEF DESCRIPTION OF THE RELEVANT LITERATURE

Kuo and Ohlrogge, *Archives of Biochem. and Biophys.* (1984) 234:290-296, describe the primary structure of spinach acyl carrier protein. Ohlrogge and Kuo, *J. Biol. Chem.* (1985) 260:8032-8037 report the existence of different isoforms of acyl carrier protein expressed differently in different tissues. Crouch et al., *J. Mol. Appl. Genet.* (1983) 2:273-283, report the synthesis of cDNA coding for napin protein.

SUMMARY OF THE INVENTION

DNA constructs are provided which provide for expression of plant acyl carrier protein. Particular constructs are produced which employ transcription initiation regions resulting in expression in plant embryos during seed maturation. The composition and amount of fatty acid can be modulated by modifying the constituents in the chloroplast or related organelle involved in a metabolic pathway in the production of fatty acids.

DESCRIPTION OF SPECIFIC EMBODIMENTS

Methods and compositions are provided for production of acyl carrier protein as an end product for use in vitro or in conjunction with seed formation of plants to provide for modified expression of fatty acids in vivo. Towards this end, DNA constructs are prepared, where the sequence encoding plant acyl carrier protein is joined to transcriptional initiation and termination regulatory regions, which are functional in a predetermined host for expression of the acyl carrier protein.

The expression constructs provide in the 5'-3' direction of transcription, a transcriptional initiation regulatory region, either constitutive or regulated, an open reading frame coding for at least a functional portion of the acyl carrier protein, desirably including a transit peptide sequence providing for translocation to the chloroplast for in vivo use, and a transcriptional termination regulatory region functional in the appropriate host.

Depending upon the host, the regulatory regions will vary. For expression in a prokaryotic or eukaryotic microorganism, particularly unicellular, host, a wide variety of constitutive or regulatable, promoters may be employed. In these instances, the primary purpose for the preparation of the acyl carrier protein is the use of the acyl carrier for protein in vitro applications.

For the most part, the constructs will involve regulatory regions functional in plants which provide for enhanced production of acyl carrier protein for enhanced and/or modification of the fatty acid composition.

The coding sequence which is employed may be derived from natural sources, synthesized, or combinations thereof. To obtain the gene from a natural source, any of a variety of plants or bacteria may be used as the source of the gene. Plants include spinach, Brassica, e.g. *campestris* or *napus*, coconut, cotton, safflower, sunflower, Cuphea etc. Among various ways in which the gene may be obtained, a library may be prepared, either genomic of cDNA. Probes may be prepared based on the amino acid sequence of the acyl carrier protein. Since it is found that there is a substantial immunological cross-reactivity between acyl carrier proteins from different sources, both prokaryotic and eukaryotic polyclonal antibodies may be employed for isolating acyl carrier proteins from a particular source and may be further used to isolate acyl carrier proteins from other plant sources. The acyl carrier protein may then be sequenced in whole or in part, and probes designed based on the peptide sequence. Where only a partial DNA sequence is obtained, the partial sequence may be satisfactory or the gene may be walked, so as to ensure that the entire coding sequence has been obtained.

Once the desired sequence has been obtained, it may be manipulated in a variety of ways. Where the sequence involves non-coding flanking regions, the flanking regions may be subjected to resection, using, for example, a nuclease such as Bal 31, restriction with a restriction endonuclease, or modification by employing in vitro mutagenesis, primer repair, or other methods for introducing mutations or lesions into the sequence. Thus, transitions, tranversions, deletions, and insertions may be performed on the naturally occurring sequence. In addition, all or a portion of the sequence may be synthesized, where one or more codons may be modified to provide for a modified amino acid sequence, or one or more codon mutations may be introduced to provide for a convenient restriction site or other purpose involved with construction or expression. The gene may be further modified by employing synthetic adaptors, linkers to introduce one or more convenient restriction sites, or the like.

The acyl carrier protein may be any one of the isozymes which may be found in a particular host, such as ACP-I and ACP-II as designated in Ohlrogge and Kuo, supra, as found in spinach, or their analogues as found in other plant hosts.

Of particular interest is the spinach acyl carrier protein, more particularly ACP-I which has the following sequence.

Spinach ACP-1

```
        HindIII
a)  1   AACTTAATATTCTTACTCAGGATAAGCTTCTCACTCTCTCTCTCTCTCTCTTACTACC      60

NcoI
a) 61   ATG GCT TCC TTG TCC GCG ACG ACA ACA GTT AGG GTT CAA CCA TCG    105
b)      MET Ala Ser Leu Ser Ala Thr Thr Thr Val Arg Val Gln Pro Ser a) 106  TCT TCG TCT CTA CAT AAA CTT AGC CAG GGG AAT GGA AGA TGT TCA    150
b)      Ser Ser Ser Leu His Lys Leu Ser Gln Gly Asn Gly Arg Cys Ser a) 151  AGT ATA GTG TGT TTG GAT TGG GGC AAA AGC AGT TTC CCA ACA CTC    195
b)      Ser Ile Val Cys Leu Asp Trp Gly Lys Ser Ser Phe Pro Thr Leu a) 196  AGG ACT TCT CGT CGT CGA TCC TTT ATC TCT GCT GCA AAG AAG GAA    240
b)      Arg Thr Ser Arg Arg Arg Ser Phe Ile Ser Ala Ala Lys Lys Glu
c)                                              Ala Lys Lys Glu a) 241  ACA ATT GAC AAA GTG TGC GAC ATT GTA AAG GAG AAA CTG GCT TTA    285
b)      Thr Ile Asp Lys Val Cys Asp Ile Val Lys Glu Lys Leu Ala Leu
c)      Thr Ile Asp Lys Val Ser Asp Ile Val Lys Glu Lys Leu Ala Leu
                                      *

PvuII
a) 286  GGA GCT GAT GTT GTG GTC ACA GCT GAT TCC GAG TTT AGT AAA CTC    330
b)      Gly Ala Asp Val Val Val Thr Ala Asp Ser Glu Phe Ser Lys Leu
c)      Gly Ala Asp Val Val Val Thr Ala Asp Ser Glu Phe Ser Lys Leu

XhoI
a) 331  GGT GCT GAT TCA TTG GAC ACG GTT GAG ATA GTG ATG AAC CTC GAG    375
b)      Gly Ala Asp Ser Leu Asp Thr Val Glu Ile Val Met Asn Leu Glu
c)      Gly Ala Asp Ser Leu Asp Thr Val Glu Ile Val Met Asn Leu Glu a) 376  GAA GAG TTC GGT ATC AAT GTG GAT GAA GAT AAA GCT CAA GAT ATA    420
b)      Glu Glu Phe Gly Ile Asn Val Asp Glu Asp Lys Ala Gln Asp Ile
c)      Glu Glu Phe Gly Ile Asn Val Asp Glu Asp Lys Ala Gln Asp Ile a) 421  TCA ACC ATC CAA CAA GCC GCC GAC GTT ATT GAG AGT CTT CTT GAG    465
b)      Ser Thr Ile Gln Gln Ala Ala Asp Val Ile Glu Ser Leu Leu Glu
c)      Ser Thr Ile Gln Gln Ala Ala Asp Val Ile Glu (-) Leu Leu Glu
                                                   * a) 466  AAG AAA TAG ACCCCAAACTATGCTCTCTCAATCAGTCAATCACCTAGCTAGGGAAT    521
b)      Lys Lys - - -
c)      Lys Lys Ala—COOH
              *

EcoRI
a) 522  GAATTC
``` a) cDNA sequence
b) amino acid sequence predicted by DNA sequence
c) amino acid sequence determined by protein sequencing (Kuo and Ohlrogge, 1984, supra)

The sequences of interest will generally have at least 300 bp usually at least about 360 bp, and desirably 411 base pairs, where the entire coding sequence includes 411 base pairs. In addition, there may be both 5' and 3' non-coding flanking regions which may extend from 1 bp to 200 bp or more from the 5' or 3' terminus of the coding region, there usually being fewer than about 100 bp, preferably fewer than about 10 bp 5' of the initiation codon, of the naturally occurring non-coding flanking region.

The open reading frame, coding for the acyl carrier protein or functional fragment thereof will be joined at its 5' end to a transcriptional initiation regulatory region. Numerous transcriptional initiation regulatory regions are available, which provide for a wide variety of constitutive or regulatable, e.g. inducible, transcription of the structural gene. Depending upon the host, transcriptional initiation regulatory regions may include regions from structural genes from viral, plasmid or chromosomal genes, or the like. Among transcriptional initiation regions which have been described are regions from bacterial and yeast hosts, such as *E. coli, Bacillus subtilis, Saccharomyces cerevisiae*, including genes such as β-galactosidase, lambda left and right promoters, glycolytic enzyme promoters, and the like. Among transcriptional initiation regions used for plants are such regions associated with the structural genes for nopaline, octopine, mannopine, ribulose-1,3-bisphosphate carboxylase, the large and small subunits, the full length promoter from cauliflower mosaic virus, napin, phaseolin, etc.

Of particular interest are those promoters which are regulated during seed maturation, particularly those synthesized in cotyledons of the embryo. These regulatory regions include regulatory regions of genes such as napin, phaseolin and glycinin. Napin regulatory regions of particular interest are from Brassica species, more particularly *campestris* and *napus*. The regulatory region will generally be at least about 150 bp and not more than about 3500 bp usually not more than about 2500 bp, and desirably not more than about 1000 bp. The napin gene has been described, Crouch, et al., supra, although there has been no disclosure of the regulatory region, nor the use of the regulatory region for an heterologous gene.

The transcriptional initiation regulatory region and coding region may be joined directly, where there are convenient restriction sites for the two regions or such restriction site(s) have been introduced, or, as appropriate, by means of synthetic adaptors or linkers. A number of regulatory regions are available as plasmids where the initiation and termination regulatory regions are separated by a polylinker, so that a number of restriction sites are available for insertion of the structural gene. These expression constructs are mostly available for microorganism hosts.

While a number of transcriptional initiation and termination regions functional in plants have been isolated, particularly from genes on the Ti- and Ri-plasmids, these regions have not achieved the level of readily available constructs including polylinkers, markers, replication systems and the like. Furthermore, for the present invention there is primary interest for expression to be regulated so that transcription is initiated in seed. For this purpose, a gene such as the napin gene is of substantial interest.

A napin regulatory region can be obtained by employing a probe which comprises a sequence adjacent 3'- or 5'-terminus or intermediate coding sequence of the structural gene for screening a genomic library of the napin host, in the case of Crouch, 1983, supra, the rapeseed host. By identifying fragments which hybridize under stringent conditions with the probe, fragments having the napin structural gene may be identified. Potential regulatory sequences 5' of the napin structural gene can be identified by restriction mapping and DNA sequence analysis. These sequences can be manipulated under various conditions to remove in whole or in part the codons coding for napin, leaving the uncoded 5' region free or substantially free of the napin coding region. In some instances, it may be desirable to remove a short non-coding region adjacent the initiation codon, usually fewer than about 20 bp, more usually fewer than about 10 bp. For further details, the experimental section should be consulted.

After joining of the open reading frame for the acyl carrier protein structural gene and the transcriptional initiation regulatory region, a functional transcriptional termination regulatory region may be present, which has been included as a result of the method for construction or one may be introduced. The termination region may be from the same structural gene as the initiation region, acyl carrier protein gene, or may be from a different structural gene, as is convenient. The termination region will usually include a terminator and sequence coding for polyadenylation.

The gene may naturally include or be modified by introducing a signal sequence for intracellular translocation, particularly to the leucoplast in seed or the chloroplast in other plant cells.

In developing the expression construct, the various components of the expression construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, resection, insertion, in vitro mutagenesis or primer repair, so as to tailor the components to the desired sequence. Once the construct has been completed, it may then be transferred to an appropriate vector for further manipulation in accordance with the manner of transformation of the plant cell.

Normally, included with the expression construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species, into which the expression construct or components thereof are introduced, one or more markers may be employed, where different conditions for selection are used for the different hosts.

The manner in which the construct is introduced into the plant host is not critical to this invention. Any method which provides for efficient transformation may be employed. Various methods include the use of Ti- or Ri-plasmids, microinjection, electroporation, liposome fusion, or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where the Agrobacterium is used for plant cell transformation, a vector may be used which may be introduced into the Agrobacterium host for homologous recombination with T-DNA of the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed host. The armed plasmid can give a mixture of normal plant cell and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al. (1980) PNAS USA, 77:7347–7351 and EPA O 120 515, which are incorporated herein by reference. Included with the expression construct and the T-DNA will be one or more markers, which allow for selection of transformed Agrobacterium and transformed plant cells. A number of markers have been developed for use with plant dells, such as resistance to chloramphenicol, the aminoglycoside G418, hygromycin, or the like. The particular marker employed is not essential to this invention, one or another marker being preferred depending on the particular host and the manner of construction.

The expression constructs may be employed with a wide variety of plant life, particularly plant life involved in the production of vegetable oils. These plants include Brassica e.g. *napus* and *campestris*, sunflower, safflower, cotton, Cuphea, soybean, and corn.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The DNA sequences can also be used as probes for searching for acyl carrier proteins in hosts other than the host from which the gene was derived. In addition, the acyl carrier protein produced in accordance with the subject invention can be used in preparing antibodies for assays for detecting acyl carrier protein. The acyl carrier protein can also be used in conjunction with chloroplast lysates to enhance the production and/or modify the composition of the fatty acids prepared in vitro. The acyl carrier protein can also be used for studying the mechanism of fatty acid formation in plants and bacteria.

The following examples are offered by way of illustration and not by way of limitation.

EXPERIMENTAL

Biological Deposits

The following DNA constructs, both transformed into *E. coli*, were deposited on the indicated date with the American Type Culture Collection, 12301 Parklawn Drive, Rockwell, Md. 20852, and have the identification and ATCC designations given below:

| Identification | ATCC Designation | Date of Deposit |
| --- | --- | --- |
| pCGN1SOL/JM83 | 67171 | July 31, 1986 |
| pCGN783/71-13 | 67868 | December 27, 1988. |

MATERIALS AND METHODS

Cloning Vectors

Cloning vectors used include the pUC vectors, pUC8 and pUC9 (Vieira and Messing, 1982) *Gene*, 19:259–268; pUC18 and pUC19 (Norrander et al., 1983) *Gene*, 26:101–106, Yanisch-Perron et al., (1985) *Gene*, 33:103–119, analogous vectors exchanging chloramphenicol resistance (CAM) as a marker for the ampicillin resistance of the pUC plasmids described above (pUC-CAM [pUC12-Cm, pUC13-Cm] Buckley, K., Ph.D. Thesis, U.C.S.D., Calif. 1985). The multiple cloning sites of pUC18 and pUC19 vectors were exchanged with those of pUC-CAM to create pCGN565 and pCGN566 which are CAM resistant. Also used were pUC118 and pUC119, which are respectively, pUC18 and pUC19 with the intergenic region of M13, from a HgiAI site at 5465 to the AhaIII site at 5941, inserted at the NdeI site of pUC. (Available from Vieira J. and Messing, J. Waksman Institute, Rutgers University, Rutgers, N.J.).

Materials

Terminal deoxynucleotide transferase (TDT), RNaseH, *E. coli*, DNA polymerase, T4 kinase, and restriction enzymes were obtained from Bethesda Research Laboratories; *E. coli* DNA ligase was obtained from New England Biolabs; reverse transcriptase was obtained from Life Sciences, Inc.; isotopes were obtained from Amersham; X-gal was obtained from Bachem, Inc. Torrance, Calif.

Construction of cDNA Library from Spinach Leaves

Total RNA was extracted from young spinach leaves in 4M guanidine thiocyanate buffer as described by Facciotti et al. (*Biotechnology* (1985) 3:241–246.). Total RNA was subjected to oligo(dT)-cellulose column chromatography two times to yield poly(A)+ RNA as described in Maniatis et al., *Molecular Cloning: A Laboratory Manual*, Cold Spring Harbor Laboratory, N.Y. (1982). A cDNA library was constructed in pUC13-Cm according to the method of Gubler and Hoffman, (*Gene* (1983) 25:263–269) with slight modifications. RNasin was omitted in the synthesis of first strand cDNA as it interfered with second strand cDNA synthesis if not completely removed, and dCTP was used to tail the vector DNA and dGTP to tail double-stranded cDNA instead of the reverse as described in the paper. The annealed cDNA was transformed to competent *E. coli* JM83 (Messing in *Recombinant DNA Technical Bulletin, NIH Publication* No. 79-99, 2 (1979) No. 2:43–48.) cells according to Hanahan (*J. Mol. Biol.* (1983) 166:557–580) and spread onto LB agar plates (Miller, Experiments in Molecular Genetics (1972) Cold Spring Harbor Laboratory, Cold Spring Harbor, N.Y.) containing 50 μg/ml chloramphenicol and 0.005% X-Gal.

Identification of Spinach ACP-I cDNA

A total of approximately 8000 cDNA clones were screened by performing Southern blots (Southern *J. Mol. Biol* (1975) 98:503) and dot blot (described below) hybridizations with clone analysis (see below) DNA from 40 pools representing 200 cDNA clones each. A 5' end-labeled synthetic oligonucleotide (ACPP4) that is at least 66% homologous with a 16 amino acid region of spinach ACP-I 5'-GATGTCTTGAGCCTTGTCCT-CATCCACATTGATACCAAACTCCTCCTC-3' is the complement to a DNA sequence that could encode the 16 amino acid peptide glu-glu-glu-phe-gly-ile-asn-val-asp-glu-asp-lys-ala-gln-asp-ile, residues 49–64 of spinach ACP-I (Kuo and Ohlrogge *Arch. Biochem. Biophys.* (1984) 234:290–296) and was used for an ACP probe.

Clone analysis DNA for Southern and dot blot hybridizations was prepared as follows. Transformants were transferred from agar plates to LB containing 50 μg/ml chloramphenicol in groups of ten clones per 10 ml media. Cultures were incubated overnight in a 37° C. shaking incubator and then diluted with an equal volume of media and allowed to grow for 5 more hours. Pools of 200 cDNA clones each were obtained by mixing contents of 20 samples. DNA was extracted from these cells as described by Birnboim and Doly (*Nucleic Acids Res.* (1979) 7:1513–1523). DNA was purified to enable digestion with restriction enzymes by extractions with phenol and chloroform followed by ethanol precipitation. DNA was resuspended in sterile, distilled water and 1 μg of each of the 40 pooled DNA samples was digested with EcoRI and HindIII and electrophoresed through 0.7% agarose gels. DNA was transferred to nitrocellulose filters following the blot hybridization technique of Southern.

ACPP4 was 5' end-labeled using $\gamma$-$^{32}$P dATP and T4 kinase according to the manufacturer's specifications. Nitrocellulose filers from Southern blot transfer of clone analysis DNA were hybridized (24 hours, 42° C.) and washed according to Berent et al. (*BioTechniques* (1985) 3:208–220). Dot blots of the same set of DNA pools were prepared by applying 1 µg of each DNA pool to nylon membrane filters in 0.5M NaOH. These blots were hybridized with the probe for 24 hours at 42° C. in 50% formamide/1% SDS/1M NaCl, and washed at room temperature in 2×SSC/0.1% SDS (1×SSC=0.15M NaCl; 0.015M Na citrate; SDS-sodium dodecylsulfate). DNA from the pool which was hybridized by the ACPP4 oligoprobe was transformed to JM83 cells and plated as above to yield individual transformants. Dot blots of these individual cDNA clones were prepared by applying DNA to nitrocellulose filters which were hybridized with the ACPP4 oligonucleotide probe and analyzed using the same conditions as for the Southern blots of pooled DNA samples.

Nucleotide Sequence Analysis

The positive clone, pCGN1SOL, was analyzed by digestion with restriction enzymes and the following partial map was obtained.

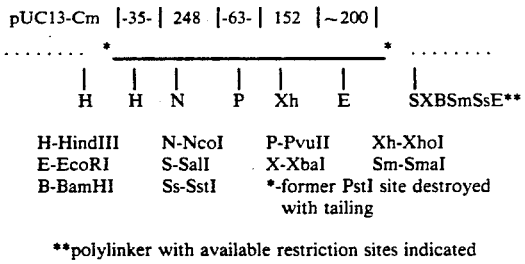

H-HindIII   N-NcoI   P-PvuII   Xh-XhoI
E-EcoRI    S-SalI   X-XbaI   Sm-SmaI
B-BamHI    Ss-SstI  *-former PstI site destroyed with tailing

**polylinker with available restriction sites indicated

The cDNA clone was subcloned into pUC118 and pUC119 using standard laboratory techniques of restriction, ligation, transformation, and analysis (Maniatis et al., (1982) supra). Single-stranded DNA template was prepared and DNA sequence was determined using the Sanger dideoxy technique (Sanger et al., *Proc. Nat. Acad. Sci.* (1977) USA 74:5463–5467). Sequence analysis was performed using a software package from IntelliGenitics, Inc.

pCGN1SOL contains an (approximately) 700 bp cDNA insert including a stretch of A residues at the 3' terminus which represents the poly(A) tail of the mRNA. An ATG codon at position 61 is presumed to encode the MET translation initiation codon. This codon is the start of a 411 nucleotide open reading frame, of which, nucleotide 229–471 encode a protein whose amino acid sequence corresponds almost perfectly with the published amino acid sequence of ACP-I of Ohlrogge and Kuo supra sequence as described previously. Discrepancies between the two amino acid sequences are indicated in the sequence set forth previously. In addition to mature protein, the pCGN1SOL also encodes a 56 residue transit peptide sequence.

Construction of a Napin Promoter

There are 298 nucleotides upstream of the ATG start codon of the napin gene on the pgN1 clone (a 3.3 kb EcoRI fragment of *B. napus* genomic DNA containing a napin gene cloned into pUC8, available from Marti Crouch, University of Indiana). pgN1 DNA was digested with EcoRI and SstI and ligated to EcoRI/SstI digested pCGN706. (pCGN706 is an XhoI/PstI fragment containing 3' and polyadenylation sequences of another napin cDNA clone pN2 (Crouch et al., 1983 supra) cloned in pCGN566 at the SalI and PstI sites.) The resulting clone pCGN707 was digested with SalI and treated with the enzyme Bal31 to remove some of the coding region of the napin gene. The resulting resected DNA was digested with SmaI after the Bal31 treatment and religated. One of the clones pCGN713, selected by size, was subcloned by EcoRI and BamHI digestion into both EcoRI/BamHI digested pEMBL18 (Dente et al., *Nucleic Acids Res.* (1983) 11:1645–1655) and pUC118 to give E418 and E4118 respectively. The extent of Bal31 digestion was confirmed by Sanger dideoxy sequencing of E418 template. The Bal31 deletion of the promoter region extended only to 57 nucleotides downstream of the start codon, thus containing the 5' end of the napin coding sequence and about 300 bp of the 5' non-coding region E4118 was tailored to delete all of the coding region of napin including the ATG start codon by in vitro mutagenesis by the method of Zoller and Smith (*Nucleic Acids Res.* (1982) 10:6487–6500) using an oligonucleotide primer 5'-GATGTTTTGTATGTGGGCCCCTAGGAGATG-3'. Screening for the appropriate mutant was done by two transformations into *E. coli* strain JM83 (Messing, J., supra) and SmaI digestion of putative transformants. The resulting napin promoter clone is pCGN778 and contains 298 nucleotides from the EcoRI site of pgN1 to the A nucleotide just before the ATG start codon of napin. The promoter region was subcloned into a chloramphenicol resistant background by digestion with EcoRI and BamHI and ligation to EcoRI/BamHI digested pCGN565 to give pCGN779c.

Extension of the Napin Promoter Clone pCGN779c contains only 298 nucleotides of potential 5'-regulatory sequence. The napin promoter was extended with 1.8 kb fragment found upstream of the 5'-EcoRI site on the original λBnNa clone. The ~3.5 kb XhoI fragment of λBnNa (available from M. Crouch), which includes the napin region, was subcloned into SalI-digested pUC119 to give pCGN930. A HindIII site close to a 5' XhoI site was used to subclone the HindIII/EcoRI fragment of pCGN930 into HindIII/EcoRI-digested Bluescript+(Vector Cloning Systems, San Diego, Calif.) to give pCGN942. An extended napin promoter was made by ligating pCGN779c digested with EcoRI and PstI and pCGN942 digested with EcoRI and PstI to make pCGN943. This promoter contains ~2.1 kb of sequence upstream of the original ATG of the napin gene contained on λBnNa.

Napin Cassette

The extended napin promoter and a napin 3'-regulatory region is combined to make a napin cassette for expressing genes seed-specifically. The napin 3' region used is from the plasmid pCGN1924 containing the XhoI/EcoRI fragment from pgN1 (XhoI site is located 18 nucleotides from the stop codon of the napin gene) subcloned into EcoRI/SalI digested pCGN565. HindIII/PstI digested pCGN943 and pCGN1924 are ligated to make the napin cassette pCGN944, with unique cloning sites SmaI, SalI and PstI for inserting genes.

Napin—ACP Construct pCGN796 was constructed by ligating pCGN1SOL digested with HindIII/BamHI, pUC8-cm digested with HindIII and BamHI and pUC118 digested with BamHI. The ACP gene from pCGN796 was transferred into a chloramphenicol background by digestion with BamHI and ligation with BamHI digested pCGN565. The resulting pCGN1902 was digested with EcoRI and SmaI and ligated to EcoRI/SmaI digested pUC118 to give pCGN1920. The ACP gene in pCGN1920 was digested at the NcoI site, filled in by treatment with the Klenow fragment, digested with SmaI and religated to form pCGN1919. This eliminated the 5'-coding sequences from the ACP gene and regenerated the ATG. This ACP gene was flanked with PstI sites by digesting pCGN1919 with EcoRI, filling in the site with the Klenow fragment and ligating a PstI linker. This clone is called pCGN945. The ACP gene of pCGN945 was moved as a BamHI/PstI fragment to pUC118 digested with BamHI and PstI to create pCGN945a so that a SmaI site (provided by the pUC118) would be at the 5'-end of the ACP sequence to facilitate cloning into the napin cassette pCGN944. pCGN945a digested with SmaI and PstI was ligated to pCGN944 digested with SmaI and PstI to produce the napin ACP cassette pCGN946. The napin ACP cassette was then transferred into the binary vector pCGN783 by cloning from the HindIII site to produce pCGN948.

Construction of pCGN783 pCGN783 is a binary plasmid containing the left and right T-DNA borders of *A. tumefaciens* (Barker et al. *Plant Mol. Biol.* (1983) 2:335–350); the gentamicin resistance gene of pPH1JI (Hirsch et al., (1984) Plasmid 12, 139–141) the 35S promoter of cauliflower mosaic virus (CaMV) (Gardner et al., *Nucleic Acids Res.* (1981) 9:2871–2890), the kanamycin resistance gene of Tn5(Jorgensen et al., infra and Wolff et al. ibid (1985) 13:355–367) and the 3' region from transcript 7 of pTiA6 (Barker et al., (1983) supra).

To obtain the gentamicin resistance marker, the gentamicin resistance gene was isolated from a 3.1 kb EcoRI-PstI fragment of pPHIJb 1and cloned into pUC9 yielding pCGN549. The HindIII-BamHI fragment containing the gentamicin resistance gene was substituted for the HindIII-BglII fragment of pCGN587 creating pCGN594.

pCGN587 was prepared as follows: The HindIII-SmaI fragment of Tn5 containing the entire structural gene for APHII (Jorgensen et al., *Mol. gen. Genet.* (1979) 177:65) was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment containing the 3'-portion of the APHII gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN564X). This procedure reassembles the APHII gene, so that EcoRI sites flank the gene. An ATG codon was upstream from and out of reading frame with the ATG initiation codon of APHII. The undesired ATG was avoided by inserting a Sau3A-PstI fragment from the 5'-end of APHII, which fragment lacks the superfluous ATG, into the BamHI-PstI site of pCGN546W to provide plasmid pCGN550.

The EcoRI fragment containing the APHII gene was then cloned into the unique EcoRI site of pCGN451, which contains an octopine synthase cassette for expression, to provide pCGN552 (1ATG).

pCGN451 includes an octopine cassette which contains about 1556 bp of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows. A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were sized fractionated, the fractions cloned and sequenced. In one case, the entire coding region and 10 bp of the 5' non-translated sequences had been removed leaving the 5' non-transcribed region, the mRNA cap site and 16 bp of the 5' non-translated region (to a BamHI site) intact. This small fragment was obtained by size fractionation on a 7% acrylamide gel and fragments approximately 130 bp long eluted.

This size fractionated DNA was ligated into M13mp9 and several clones sequenced and the sequence compared to the known sequence of the octopine synthase gene. The M13 construct was designated p14, which plasmid was digested with BamHI and EcoRI to provide the small fragment which was ligated to XhoI to BamHI fragment containing upstream 5' sequences from pTiA6 (Garfinkel and Nester, *J. Bacteriol.* (1980) 144:732) and to an EcoRI to XhoI fragment containing the 3' sequences.

The resulting XhoI fragment was cloned into the XhoI site of the pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,500 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence). pCGN451 also provides the right T-DNA border.

The resulting plasmid pCGN451 having the ocs 5' and the ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation.

This ocs/KAN gene was used to provide a selectable marker for the trans type binary vector pCGN587.

The 5' portion of the engineered octopine synthase promoter cassette consists of the pTiA6 DNA from the XhoI at bp 15208-13644 (Barker's numbering), which also contains the T-DNA boundary sequence (border) implicated in T-DNA transfer. In the plasmid pCGN587, the ocs/KAN gene from pCGN552 provides a selectable marker as well as the right border. The left boundary region was first cloned in M13mp9 as a HindIII-SmaI piece (pCGN502) (base pairs 602-2213) and recloned as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglII fragment of pVCK102 (Knauf and Nester, *Plasmid* (1982) 8:45), creating pCGN585. By replacing the smaller SalI fragment of pCGN585 with the XhoI fragment from pCGN552 containing the ocs/KAN gene, pCGN587 was obtained.

The pCGN594 HindIII-BamHI region, which contains an 5'-ocs-kanamycin-ocs-3' (ocs is octopine synthase with 5' designating the promoter region and 3' the terminator region, see U.S. application Ser. No. 775,923, filed Sep. 13, 1985) fragment was replaced with the HindIII-BamHI polylinker region from pUC18.

pCGN566 contains the EcoRI to HindIII polylinker of pUC18 inserted into the EcoRI-HindIII sites of pUC13-Cm. The HindIII-BglII fragment of pNW31C-8,29-1 (Thomashow et al., *Cell* (1980) 19:729) containing ORF1 and -2 of pTiA6 was subcloned into the HindIII-BamHI sites of pCGN566 producing pCGN703.

The Sau3A fragment of pCGN703 containing the 3' region of transcript 7 (corresponding to bases 2396-2920 of pTiA6 (Barker et al., (1983) supra) was subcloned into the BamHI site of pUC18 producing pCGN709. The EcoRI-SmaI polylinker region of pCGN709 was substituted with the EcoRI-SmaI fragment of pCGN587, which contains the kanamycin resistance gene (APH3-II) producing pCGN726.

The EcoRI-SalI fragment of pCGN726 plus the BglII-EcoRI fragment of pCGN734 were inserted into the BamHI-SalI site of pUC8-Cm producing pCGN738. pCGN726c is derived from pCGN738 by deleting the 900 bp EcoRI-EcoRI fragment.

To construct pCGN167, the AluI fragment of CaMV (bp 7144-7735) (Gardner et al., (1981) supra) was obtained by digestion with AluI and cloned into the HincII site of M13mp7 (Messing, et al., *Nucl. Acid. Res.* (1981) 9:309-321) to create C614. An EcoRI digest of C614 produced the EcoRI fragment from C614 containing the 35S promoter which was cloned into the EcoRI site of pUC8 (Vieira and Messing et al., *Gene* (1982) 19:259) to produce pCGN146.

To trim the promoter region, the BglII site (bp 7670) was treated with BglII and resected with Bal31 and subsequently a BglII linker was attached to the Bal31 treated DNA to produce pCGN147.

pCGN148a containing a promoter region, selectable marker (KAN with 2ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., *Mol. gen. Genet.* (1979) 177:65) with HindIII-BamHI and inserting the HindIII-BamHI fragment containing the kanamycin gene into the HindIII-BamHI sites in the tetracycline gene of pACYC184 (Chang & Cohen, *J. Bacteriol.* (1978) 134:1141-1156). pCGN526 was made by inserting the BamHI fragment 19 of pTiA6 (Thomashow et al., *Cell* (1980) 19:729-739), modified with XhoI linkers inserted into the SmaI site, into the BamHI site of pCGN525. pCGN528 was obtained by deleting the small XhoI fragment from pCGN526 by digesting with XhoI and religating.

pCGN149a was made by cloning the BamHI-kanamycin gene fragment from pMB9KanXXI into the BamHI site of pCGN148a.

pMB9KanXXI is a pUC4K variant (Vieira and Messing, *Gene* (1982) 19:259-268) which has the XhoI site missing but contains a functional kanamycin gene from Tn903 to allow for efficient selection in Agrobacterium.

pCGN149a was digested with BglII and SphI. This small BglII-SphI fragment of pCGN149a was replaced with the BamHI-SphI fragment from MI (see below) isolated by digestion with BamHI and SphI. This produces pCGN167, a construct containing a full length CaMV promoter, 1ATG-kanamycin gene, 3' end and the bacterial Tn903-type kanamycin gene. MI is an EcoRI fragment from pCGN546X (see construction of pCGN587) and was cloned into the EcoRI cloning site of M13 mp9 in such a way that the PstI site in the 1ATG-kanamycin gene was proximal to the polylinker region of M13mp9.

The HindIII-BamHI fragment in the pCGN167 containing the CaMV-35S promoter, 1ATG-kanamycin gene and the BamHI-fragment 19 to pTiA6 was cloned into the BamHI-HindIII sites of pUC19 creating pCGN976. The 35S promoter and 3' region from transcript 7 was developed by inserting a 0.7 kb HindIII-EcoRI fragment of pCGN976 (35S promoter) and the 0.5 kb EcoRI-SalI fragment of pCGN709 (transcript 7:3') into the HindIII-SalI sites of pCGN566 creating pCGN766c.

The 0.7 kb HindIII-EcoRI fragment of pCGN766c (CaMV-35S promoter) was ligated to the 1.5 kb EcoRI-SalI in pCGN726c (1ATG-KAN 3' region) into the HindIII-SalI sites of pUC119 to produce pCGN778. The 2.2 kb region of pCGN778, HindIII-SalI fragment containing the CaMV-35S promoter and 1ATG-KAN-3' region was used to replace the HindIII-SalI linker region of pCGN739 to produce pCGN783.

pCGN948 was introduced into *Agrobacterium tumefaciens* EHA101 (Hood et al., *J. Bacteriol.* (1986) 168:1291-1301) by transformation. An overnight two ml culture of EHA101 was grown in MG/L broth at 30° C. 0.5 ml was inoculated into 100 ml of MG/L broth (Garfinkel and Nester, *J. Bacteriol.* (1980) 144:732-743) and grown in a shaking incubator for 5 h at 30° C. The cells were pelleted by centrifugation at 7K., resuspended in 1 ml of MG/L broth and placed on ice. Approximately one μg of pCGN948 DNA was placed in 100 μl of MG/L broth to which 200 μl of the EHA101 suspension was added; the tube containing the DNA-cell mix was immediately placed into a dry ice/ethanol bath for 5 minutes. The tube was quick thawed by 5 minutes in a 37° C. water bath followed by 2 h shaking at 30° C. after adding 1 ml of fresh MG/L medium. The cells were pelleted and spread onto MG/L plates (1.5% agar) containing 100 mg/l gentamicin. Plasmid DNA was isolated from individual gentamicin-resistant colonies, transformed back into *E. coli*, and characterized by restriction enzyme analysis to verify that the gentamicin-resistance EHA101 contained intact copies of pCGN948. Single colonies are picked and purified by two more streakings on MG/L plates containing 100 mg/l gentamicin.

Seeds of *Brassica napus* cv. Westar were soaked in 95% ethanol for 4 minutes. They were sterilized in 1% solution of sodium hypochlorite with 50 μl of "Tween 20" surfactant per 100 ml sterilent solution. After soaking for 45 minutes, seeds were rinsed 4 times with sterile distilled water. They were planted in sterile plastic boxes 7 cm wide, 7 cm long, and 10 cm high (Magenta) containing 50 ml of 1/10th concentration of MS (Murashige minimal organics medium, Gibco) with added pyridoxine (50 μg/l) nicotinic acid (50 μg/l), glycine (200 μg/l) and solidified with 0.6% agar. The seeds germinated and were grown at 22° C. in a 16h-8h light-dark cycle with light intensity approximately 65 μEm$^{-2}$s$^{-1}$. After 5 days, the seedlings were taken under sterile conditions and the hypocotyls excised and cut into pieces of about 4 mm in length. The hypocotyl segments were placed on a feeder plate or without the feeder layer on top of a filter paper on the solidified B5 0/1/1 or B5 0/1/0 medium. B5 0/1/0 medium contains B5 salts and vitamins (Gamborg, Miller and Ojima, *Experimental Cell Res.* (1968) 50:151-158), 3% sucrose, 2,4-dichlorophenoxyacetic acid (1.0 mg/l), pH adjusted to 5.8, and the medium is solidified with 0.6% Phytagar; B5 0/1/1 is the same with the addition of 1.0 mg/l kinetin. Feeder plates were prepared 24 hours in advance by pipetting 1.0 ml of a stationary phase tobacco suspension culture (maintained as described in Fillatti et al., *Mol. gen. Genet.* (1987) 206:192-199) onto B5 0/1/0 to B5 0/1/1 medium. Hypocotyl segments were cut and placed on feeder plates 24 hours prior to Agrobacterium treatment. *Agrobacterium tumefaciens* (strain EHA101×948) were prepared by incubating a single colony of Agrobacterium in MG/L broth at 30° C. Bacteria were harvested 16 hours later and dilutions of $10^8$ bacteria per ml were prepared in MG/L broth. Hypocotyl segments were inoculated with bacteria by placing in Agrobacterium suspension and allowed to sit for 30-60 minutes, then removed and transferred to Petri plates containing B5 0/1/1 or 0/1/0 medium described above. The plates were incubated in low light at 22° C. The co-incubation of bacteria with the hypocotyl segments took place for 24-48 hours. The hypocotyl segments were removed and placed on B5 0/1/1 or 0/1/0 containing 500 mg/l carbenicillin (kanamycin sulfate at 10, 25, or 50 mg/l was sometimes added at this time) for 7 days in continuous light approximately 65 μEm$^{-2}$S$^{-1}$) at 22° C. They were transferred to B5 salts medium containing 1% sucrose, 3 mg/l benzylaminopurine and 1 mg/l zeatin. This was supplemented with 500 mg/l carbenicillin, 10, 25, or 50 mg/l kanamycin sulfate, and solidified with 0.6% Phytagar (Gibco). Thereafter explants were transferred to fresh medium every 2 weeks.

After 1 month green shoots developed from green calli which were selected on media containing kanamycin. Shoots continued to develop for 3 months. The shoots were cut from the calli when they were at least 1 cm high and placed on B5 medium with 1% sucrose, no added growth substances, 300 mg/l carbenicillin, and solidified with 0.6% phytagar. The shoots continued to grow and several leaves were removed to test for neomycin phosphotransferase II (NPTII) activity. Shoots which were positive for NPTII activity were placed in Magenta boxes containing B5 0/1/1 medium with 1% sucrose, 2 mg/l indolebutyric acid, 200 mg/l carbenicillin, and solidified with 0.6% Phytagar. After a few weeks the shoots developed roots and were transferred to soil. The plants were grown in a growth chamber at 22° C. in a 16-8 hours light-dark cycle with light intensity 220 μEm$^{-2}$s$^{-1}$ and after several weeks were transferred to the greenhouse.

SOUTHERN DATA

Regenerated *B. napus* plants from cocultivations of *Agrobacterium tumefaciens* EHA101 containing pCGN948 and *B. napus* hypocotyls were examined for proper integration and embryo-specific expression of the spinach leaf ACP gene. Southern analysis was performed using DNA isolated from leaves of regenerated plants by the method of Dellaporta et al. (*Plant Mol. Biol. Rep.* (1983) 1:19-21) and purified once by banding in CsCl. DNA (10 μg) was digested with the restriction enzyme EcoRI, electrophoresed on a 0.7% agarose gel and blotted to nitrocellulose (see Maniatis et al., 1982, supra). Blots were probed with pCGN945 DNA containing 1.8 kb of the spinach ACP sequence or with the EcoRI/HindIII fragment isolated from pCGN936c (made by transferring the HindIII/EcoRI fragment of pCGN930 into pCGN566) containing the napin 5' sequences labeled with $^{32}$P-dCTP by nick translation (described by the manufacturer, BRL Nick Translation Reagent Kit, Bethesda Research Laboratories, Gaithersburg, Md.). Blots were prehybridized and hybridized in 50% formamide, 10×Denhardt's, 5×SSC, 0.1% SDS, 5 mM EDTA, 100 μg/ml calf thymus DNA and 10% dextran sulfate (hybridization only) at 42° C. (Reagents described in Maniatis et al., (1982) supra). Washes were in 1×SSC, 0.1% SDS, 30 min and twice in 0.1×SSC, 0.1% SDS at 55° C.

Autoradiograms showed two bands of approximately 3.3 and 3.2 kb hybridized in the EcoRI digests of DNA from four plants when probed with the ACP gene (pCGN945) indicating proper integration of the spinach leaf ACP construct in the plant genome since 3.3 and 3.2 kb EcoRI fragments are present in the T-DNA region of pCGN948. The gene construct was present in single or multiple loci in the different plants as judged by the number of plant DNA-construct DNA border fragments detected when probed with the napin 5' sequences.

NORTHERN DATA

Expression of the integrated spinach leaf ACP gene from the napin promoter was detected by Northern analysis in seeds but not leaves of one of the transformed plants shown to contain the construct DNA. Developing seeds were collected from the transformed plant 21 days post-anthesis. Embryos were dissected from the seeds and frozen in liquid nitrogen. Total RNA was isolated from the seed embryos and from leaves of the transformed plant by the method of Crouch et al. (1983) supra), electrophoresed on formaldehyde-containing 1.5% agarose gels as described (Shewmaker et al., *Virology* (1985) 140:281-288) and blotted to nitrocellulose (Thomas, *Proc. Natl. Acad. Sci.*, U.S.A. (1980) 77:5201-5205). Blots were prehybridized, hybridized and washed as described above. The probe was an isolated PstI/BamHI fragment from pCGN945 containing only spinach leaf ACP sequences labeled by nick translation.

An RNA band of ~0.8 kb was detected in embryos but not leaves of the transformed plant indicating seed-specific expression of the spinach leaf ACP gene.

Although higher plant fatty acid biosynthetic genes have been shown to recognize acyl-ACP substrates when the ACP moiety is an *Escherichia coli* ACP, it remains possible that different forms of ACP from different sources may affect the efficiency and/or the final products of fatty acid synthesis in vivo. For instance both spinach (Ohlrogge and Kuo, . *Biol. Chem.* (1985) 260:8032–8037) and barley (Hoj and Svendsen, *Carlsberg. Res. Commun.* (1984) 49:483–492, contain more than one form of ACP. To support the generality of using isoforms of ACP to enhance the value of oilseed crops, a cDNA copy of the gene for an ACP found in the seeds of the oilseed crop turnip rape (*Brassica campestris*) was isolated and characterized.

The following is the procedure for integrating the ACP gene into a chimeric gene using a napin promoter from *Brassica campestris* rather than *Brassica napus*.

Immature seeds are collected from *Brassica campestris* cv. "R-500", a self-compatible variety of turnip rape. Whole seeds are collected at stages corresponding approximately to 14 to 28 days after flowering. RNA isolation and preparation of a cDNA bank was as described above for the isolation of a spinach ACP cDNA clone. To probe the cDNA bank, the oligonucleotide (5')-ACTTTCTCAACTGTCTCTGGTTTAG-CAGC-(3') was synthesized using an Applied Biosystems DNA Synthesizer, model 380A, according to manufacturer's recommendations. This synthesis DNA molecule will hybridize at low stringencies to DNA or RNA sequences coding for the amino acid sequence (ala-ala-lys-pro-glu-thr-val-glu-lys-val). This amino acid sequence has been reported for ACP isolated from the sees of *Brassica napus* (Slabas et al., 7th International Symposium of the Structure and Function of Plant Lipids, University of California, Davis, Calif., Plenum Press, N.Y. 1987); the ACP from *B. campestris* seed is highly homologous. Approximately 2200 different cDNA clones are analyzed using a colony hybridization technique (Taub and Thompson, *Anal. Biochem.* (1982) 126:222–230) and hybridization conditions corresponding to (Wood et al., *Proc. Natl. Acad. Sci. U.S.A.* (1985) 82:1585–1588). DNA sequence analysis of two cDNA clones showing obvious hybridization to the oligonucleotide probe indicated that one, designated pCGN1Bcs, coded for an ACP-precursor protein as evidenced by the considerable homology of the encoded amino acid sequence with ACP proteins described from *Brassica napus* (Slabas et al., supra). The DNA sequence of pCGN1Bcs (referred to also as AGB1) is indicated as follows:

AGB1 CDNA

```
                                          TthIIII
                                          TaqI
    XhoI                                  SalI
    TaqI    Sau3AI                        HincII
    AvaI    BglII    AvaI       TaqI      AccI
    | |     |        |          |         | | |
  1 TCTCGAGCAGATCTCTCTCGGGAATATCGACAATGTCGACCACTTTCTGCTCTTCCGTCTCCATGCAAG    69
                                     METSer Thr Thr Phe Cys Ser Ser Val Ser METGln A
    3       10       18         28        37
    4       10                             35
    3                                      36
                                           33
```

```
                                                            AluI
                                                            |
 70 CCACTTCTCTGGCAGCAACAACGAGGATTAGTTTCCAGAAGCCAGCTTTGGTTTCAACGACTAATCTCT    138
    la Thr Ser Leu Ala Ala Thr Thr Arg Ile Ser Phe Gln Lys Pro Ala Leu Val Ser Thr Thr Asn Leu S
                                                       115
```

```
                                                  HhaI
                                                    HaeIII
                                                  |  |
139 CCTTCAACCTCCGCCGTTCAATCCCCACTCGTTTCTCAATCTCCTGCGCGGCCAAACCAGAGACGGTTG    207
    er Phe Asn Leu Arg Arg Ser Ile Pro Thr Arg Phe Ser Ile Ser Cys Ala Ala Lys Pro Glu Thr Val G
                                                                190
                                                       187
```

```
          DdeI                            AluI
          |                               |
208 AGAAAGTGTCTAAGATAGTTAAGAAGCAGCTATCACTCAAAGACGACCAAAAGGTCGTTGCGGAGACCA    276
    lu Lys Val Ser Lys Ile Val Lys Lys Gln Leu Ser Leu Lys Asp Asp Gln Lys Val Val Ala Glu Thr L
                218                       237
```

```
          Sau3AI         HinfI    TaqI
          |              |        |
277 AGTTTGCTGATCTTGGAGCAGATTCTCTCGACACTGTTGAGATAGTGATGGGTTTAGAGGAAGAGTTTG    345
    ys Phe Ala Asp Leu Gly Ala Asp Ser Leu Asp Thr Val Glu Ile Val METGly Leu Glu Glu Glu Phe A
                285            298      305
```

```
    TaqI                       DdeI
    EcoRV                      AluI                              AluI
    | |                        | |                               |
346 ATATCGAAATGGCTGAAGAGAAAGCTCAGAAGATTGCTACTGTGGAGGAAGCTGCTGAACTCATTGAAG    414
    sp Ile Glu METAla Glu Glu Lys Ala Gln Lys Ile Ala Thr Val Glu Glu Ala Ala Glu Leu Ile Glu G
        348                        370                              397
        350                        371
```

-continued
AGB1 CDNA

```
       SacI
       AluI
       | |
415 AGCTCGTTCAACTTAAGAAGTAATTTTAGTATTAAGAGCAGCCAAGGCTTTGTTGGGTTTGTTGTTTTC       483
    lu  Leu Val Gln Leu Lys Lys
       417
          419
```

```
                                              HinfI              DraI
                                              |                  |
484 ATAATCTTCCTGTCATTTTCTTTTTCTTTAATGTGTCAAGCGACTCTGTTGGTTTAAAGTAGTATCTGT       552
                                              526          539
```

```
553 TTGCCAAAAAAA                                                                 564
```

To achieve high-level embryo-specific expression of a *Brassica campestris* seed ACP in a transgenic *Brassica napus*, a chimeric gene is made analogous to the embryo-specific chimeric gene employing spinach ACP-coding DNA sequences as described for pCGN946 above. The pCGN1Bcs ACP-coding region is adapted to fit into the *Brassica campestris* napin-type promoter element present in pCGN1803 (described below).

CONSTRUCTION OF *B. CAMPESTRIS* NAPIN PROMOTER CASSETTE

A BglII-partial genomic library ob *B. campestris* DNA was made in the lambda vector Charon 35 using established protocols (Maniatis et al., (1982) supra). The titer of the amplified library was ~1.2×10⁸ phage/ml. Four hundred thousand recombinant bacteriophage were plated at a density of 10⁵ per 9×9 NZY plate (NZYM as described in Maniatis et al., 1982 supra) in NZY+10 mM MgSO₄+0.9% agarose after adsorption to DH1 *E coli* cells (Hanahan, D., *J. Mol. Biol.* (1983) 166:557) for 20 min at 37° C. Plates were incubated at 37° C. for ~13 hours, cooled at 4° C. for two and one half hours and phage were lifted onto GeneScreen Plus (New England Nuclear) by laying precut filters over the plates for approximately 1 min and peeling them off. The adsorbed phage DNA was immobilized by floating the filter on 1.5M Nacl, 0.5M NaOH for 1 min., neutralizing in 1.5M NaCl, 0.5M Tris-HCl, pH 8.0 for 2 min and 2XSSC for 3 min. Filters were air dried until just damp, prehybridized and hybridized at 42° C. as described for Southern analysis. Filters were probed for napin-containing clones using an XhoI/SalI fragment of the cDNA clone BE5 which was isolated from the *B. campestris* seed cDNA library described above using the probe pN1 (Crouch et al., 1983. supra). Three plaques were hybridized strongly on duplicated filters and were plaque purified as described (Maniatis et al., 1982 supra).

The following is the BE5 cDNA sequence.

```
                            BE5 CDNA
                          LENGTH = 734

AluI
               |
  1 ACAGAACATACACAAATGGCGAACAAGCTCTTCCTCGTCTCGGCAACTCTCGCCTTGTTCTTCCTTCTC        69
    Thr Glu His Thr Gln METAla Asn Lys Leu Phe Leu Val Ser Ala Thr Leu Ala Leu Phe Phe Leu Leu
                              28
```

```
                                   TaqI
                                   SalI
                                   HincII                           NaeI
              AccI                  AccI                            HpaII
              | |                   | | |                           | | |
                                                                    HaeIII
 70 ACCAATGCCTCCGTCTACAGGACGGTTGTGGAAGTCGACGAAGATGATGCCACAAATCCAGCCGGCCCA        138
    Thr Asn Ala Ser Val Tyr Arg Thr Val Val Glu Val Asp Glu Asp Asp Ala Thr Asn Pro Ala Gly Pro
                 84                        105                          135
                                           103                132
                                           104                133
                                           105
```

```
                                                            HindIII
                                                            AluI
                                                            | |
139 TTTAGGATTCCAAAATGTAGGAAGGAGTTTCAGCAAGCACAACACCTGAAAGCTTGCCAACAATGGCTC        207
    Phe Arg Ile Pro Lys Cys Arg Lys Glu Phe Gln Gln Ala Gln His Leu Lys Ala Cys Gln Gln Trp Leu
                                                                 191
                                                             189
```

```
                                              AvaII
             HpaII     AvaII     AluI      TaqI
             |         |         | |       |
208 CACAAGCAGGCAATGCAGTCCGGTAGTGGTCCAAGCTGGACCCTCGATGGTGAGTTTGATTTTGAAGAC        276
    His Lys Gln Ala METGln Ser Gly Ser Gly Pro Ser Trp Thr Leu Asp Gly Glu Phe Asp Phe Glu Asp
                   228           236     243         252
                                     246
```

-continued
BE5 CDNA
LENGTH = 734

```
                                                                                   SacI
             HaeIII                    HaeIII                                      AluI
               |                         |                                          |
277 GACGTGGAGAACCAACAACAGGGCCCGCAGCAGAGGCCACCGCTGCTCCAGCAGTGCTGCAACGAGCTC    345
    Asp Val Glu Asn Gln Gln Gln Gly Pro Gln Gln Arg Pro Pro Leu Leu Gln Gln Cys Cys Asn Glu Leu
                            300                 313                              343
                                                                                 345
```

```
    BstNI
     |
346 CACCAGGAAGAGCCACTTTGCGTTTGCCCAACCTTGAAAGGAGCATCCAAAGCCGTTAAACAACAGATT     414
    His Gln Glu Glu Pro Leu Cys Val Cys Pro Thr Leu Lys Gly Ala Ser Lys Ala Val Lys Gln Gln Ile
         350
```

```
    TaqI
     |
415 CGACAACAACAGGGACAACAAATGCAGGGACAGCAGATGCAGCAAGTGATTAGCCGTATCTACCAGACC    483
    Arg Gln Gln Gln Gly Gln Gln METGln Gly Gln Gln METGln Gln Val Ile Ser Arg Ile Tyr Gln Thr
    415
```

```
                  AluI                                                             BstNI
                   |                                                                 |
484 GCTACGCACTTACCTAGAGCTTGCAACATCAGGCAAGTTAGCATTTGCCCCTTCCAGAAGACCATGCCT    552
    Ala Thr His Leu Pro Arg Ala Cys Asn Ile Arg Gln Val Ser Ile Cys Pro Phe Gln Lys Thr METPro
                       503                                                         552
```

```
                       XhoI
    HpaII              TaqI
    HaeIII             AvaI           AccI
     | |                | |            |
553 GGGCCCGGCTTCTACTAGATTCCAAACGAATATCCTCGAGAGTGTGTATACCACGGTGATATGAGTGTG    621
    Gly Pro Gly Phe Tyr .
        556                            588    600
        558                            589
                                       588
```

```
    HincII                                         RsaI
     |                                              |
622 GTTGTTGATGTATGTTAACACTACATAGTCATGGTGTGTGTTCCATAAATAATGTACTAATGTAATAAG    690
              635                                          677
```

```
    AccI                              DraI
     |                                 |
691 AACTACTCCGTAGACGGTAATAAAAGAGAAGTTTTTTTTTTTAA                              734
         702                            733
```

One of the clones named lambda CGN1-2 was restriction mapped, and the napin gene was localized to overlapping 2.7 kb XhoI and 2.1 kb SalI restriction fragments. The two fragments were subcloned from lambda CGN1-2DNA into pCGN789 (a pUC based vector the same as pUC119 with the normal polylinker replaced by the synthetic linker—5' GGAATTCGT-CGACAGATCTCTGCAGCTCGAGGGATC-CAAGCTT 3'—which represents the polylinker EcoRI, SalI, BglII, PstI, XhoI, BamHI, HindIII). The identity of the subclones as napin was confirmed by sequencing. The entire coding region sequence as well as extensive 5' upstream and 3' downstream sequences were determined.

Lambda CGN1-2
NCG-186 Linear
LENGTH = 4325

```
    XhoI
    TaqI
    AvaI                                              HindIII
     | |                                               AluI          TaqI
     | |                                                | |           |
  1 CTCGAGGCAGTCACTAACATGAAGTTTGACGAGGAGCCCAACTATGGGAAGCTTATTTCTCTTTTCGAT    69
    2                                                   52            66
     3                                                  50
    2
```

```
                                                       SacI
    HhaI   XbaI                                        AluI
     |      |                                           | |
 70 ACTCTAATTGAGCCGTGCGCTCTATCTAGACCAATTAGAATTGATGGAGCTCTAAAGGTTGCTGGCTGT   138
            89    95                                   119
                                                       121
```

-continued
Lambda CGN1-2
NCG-186 Linear
LENGTH = 4325

```
            NdeI                                                    NdeI
             |                                                       |
139  TTTCTTGTTCATATGATTAACTTCTAAACTTGTGTATAAATATTCTCTGAAAGTGCTTCTTTTGGCATA    207
             150                                                    206

208  TGTAGGTTGGGCAAAAACGAGGAAGATTGCTTCTCAATTTGGAAGAGGATGAACAGCCGAAGAAGAAAA    276

Sau3AI
                              DdeI
277  TAAGAATAGGCAGTCCTGCTACTCAATGGATCTCAGTCTATAACGGTCGTCGTCCCATGAAACAGAGGT    345
                                309
                              305

EcoRV
                                                                 |
346  AAAACATTTTTTGCATATACACTTTGAAAGTTCCTCACTAACTGTGTAATCTTTTGGTAGATATCACTA    414
                                                                    408

HincII
              HhaI
              HaeIII
              DdeI
              BstEII
              BalI                                  HaeIII         AluI
              | | |                                   |             |
415  CAATGTCGGAGAGACAA3GGCTGMNCANCATATACAAAAGGGAAATGAAGATGGCCTTTTGATTAGCTG    483
              439                                   469           481
              438
              439
              439
              440
              438

AluI                                   HinfI
                 |                                       |
484  TGTAGCATCAGCAGCTAATCTCTGGGCTCTCATCATGGATGCTGGAACTGGATTCACTTCTCAAGTTTA    552
                498                                    535

MspI
      HpaII                                           HinfI
       |                                                |
553  TGAGTTGTCACCGGTCTTCCTACACAAGGTAATAATCAGTTGAAGCAATTAAGAATCAATTTGATTTGT    621
       564                                            606
       564

DdeI
       |
622  AGTAAACTAAGAAGAACTTACCTTATGTTTTCCCCGCAGGACTGGATTATGGAACAATGGGAAAAGAAC    690
       629

SacI
        AluI        AluI                      AluI
         |           |                        | |
691  TACTATATAAGCTCCATAGCTGGTTCAGATAACGGGAGCTCTTTAGTTGTTATGTCAAAAGGTTAGTGT    759
         702        710                       729
                                                731

760  TTAGTGAATAATAAACTTATACCACAAAGTCTTCATTGACTTATTTATATACTTGTTGTGAATTGCTAG    828

DdeI                HinfI
            |                    |
829  GAACTACTTATTCTCAGCAGTCATACAAAGTGAGTGACTCATTTCCGTTCAAGTGGATAAATAAGAAAT    897
            842                865

XmnI                                                         TaqI
       |                                                            |
898  GGAAAGAAGATTTTCATGTAACCTCCATGACAACTGCTGGTAATCGTTGGGGTGTGGTAATGTCGAGGA    966
       908                                                         961
```

-continued
Lambda CGN1-2
NCG-186 Linear
LENGTH = 4325

```
             Sau3AI
             BclI
              |
967  ACTCTGGCTTCTCTGATCAGGTAGGTTTTTGTCTCTTATTGTCTGGTGTTTTTATTTTCCCCTGATAGT  1035
              981
              981

AluI          RsaI
                                        |             |
1036 CTAATATGATAAACTCTGCGTTGTGAAAGGTGGTGGAGCTTGACTTTTTGTACCCAAGCGATGGGATAC  1104
                                       1074         1087

Sau3AI      AluI
                                                    |          |
1105 ATAGGAGGTGGGAGAATGGGTATAGAATAACATCAATGGCAGCAACTGCGGATCAAGCAGCTTTCATAT  1173
                                                  1155       1165

ScaI
                                          HinfI                 RsaI
                                            |                    |
1174 TAAGCATACCAAAGCGTAAGATGGTGGATGAAACTCAAGAGACTCTCCGCACCACCGCCTTTCCAAGTA  1242
                                          1215                  1242
                                                                1242

AluI              Sau3AI                        DdeI
               |                   |                            |
1243 CTCATGTCAAGGTTGGTTTCTTTAGCTTTGAACACAGATTTGGATCTTTTTGTTTTGTTTCCATATACT  1311
              1268               1285                         1311

AvaII DdeI   AluI                              HinfI    RsaI
      |    |      |                                   |       |
1312 TAGGACCTGAGAGCTTTTGGTTGATTTTTTTTTCAGGACAAATGGGCGAAGAATCTGTACATTGCATCA  1380
     1315       1325                                1363    1370
           1319

1381 ATATGCTATGGCAGGACAGTGTGCTGATACACACTTAAGCATCATGTGGAAAGCCAAAGACAATTGGAG  1449

HinfI
       DdeI
      | |
1450 CGAGACTCAGGGTCGTCATAATACCAATCAAAGACGTAAAACCAGACGCAACCTCTTTGGTTGAATGTA  1518
        1456
     1454

RsaI
                   |
1519 ATGAAAGGGATGTGTCTTGGTATGTATGTACGAATAACAAAAGAGAAGATGGAATTAGTAGTAGAAATA  1587
                  1548

AluI                                    EcoRV
         |                                        |
1588 TTTGGGAGCTTTTTAAGCCCTTCAAGTGTGCTTTTTATCTTATTGATATCATCCATTTGCGTTGTTTAA  1656
        1596                                    1635

XbaI               DdeI
      |                  |
1657 TGCGTCTCTAGATATGTTCCTATATCTTTCTCAGTGTCTGATAAGTGAAATGTGAGAAAACCATACCAA  1725
        1664            1687

HinfI
                             |
1726 ACCAAAATATTCAAATCTTATTTTTAATAATGTTGAATCACTCGGAGTTGCCACCTTCTGTGCCAATTG  1794
                            1761

HinfI                                                    EcoRI
      |                                                         |
1795 TGCTGAATCTATCACACTAGAAAAAAACATTTCTTCAAGGTAATGACTTGTGGACTATGTTCTGAATTC  1863
        1800                                                  1859
```

-continued
Lambda CGN1-2
NCG-186 Linear
LENGTH = 4325

```
1864  TCATTAAGTTTTTATTTTCTGAAGTTTAAGTTTTTACCTTCTGTTTTGAAATATATCGTTCATAAGATG        1932

SphI
          BstNI       AluI                       Sau3AI
            |          |                          | |
1933  TCACGCCAGGACATGAGCTACACATCGCACATAGCATGCAGATCAGGACGATTTGTCACTCACTTCAAA        2001
         1940        1950                1973
                                    1971

SphI
      DdeI    AluI             HhaI    NdeI    NsiI            Sau3AI
        |      |                |       |       |                |
2002  CACCTAAGAGCTTCTCTCTCACAGCGCACACACATATGCATGCAATATTTACACGTGATCGCCATGCAA        2070
        2006   2012            2028    2036   2042             2058
                                              2044

2071  ATCTCCATTCTCACCTATAAATTAGAGCCTCGGCTTCACTCTTTACTCAAACCAAAACTCATCACTACA        2139

AluI
                         |
2140  GAACATACACAAATGGCGAACAAGCTCTTCCTCGTCTCGGCAACTCTCGCCTTGTTCTTCCTTCTCACC        2208
                       METAla Asn Lys Leu Phe Leu Val Ser Ala Thr Leu Ala Leu Phe Phe Leu Leu Thr
                                                  2164

TaqI                              NaeI
                                      SalI                              MspI
                                      HincII                            HpaII
           AccI                       AccI                              HaeIII
             |                        |·| |                             | | |
2209  AATGCCTCCGTCTACAGGACGGTTGTGGAAGTCGACGAAGATGATGCCACAAATCCAGCCGGCCCATTT     2277
      Asn Ala Ser Val Tyr Arg Thr Val Val Glu Val Asp Glu Asp Asp Ala Thr Asn Pro Ala Gly Pro Phe
                       2220                    2241                        2771
                                               2239                        2268
                                               2240                        2268
                                               2241                        2269

HindIII
      HinfI                                                     AluI
        |                                                        | |
2278  AGGATTCCAAAATGTAGGAAGGAGTTTCAGCAAGCACAACACCTGAAAGCTTGCCAACAATGGCTCCAC    2346
      Arg Ile Pro Lys Cys Arg Lys Glu Phe Gln Gln Ala Gln His Leu Lys Ala Cys Gln Gln Trp Leu His
                2281                                         2327
                                                             2325

MspI               AvaII
              HpaII    AvaII     AluI      TaqI
                |        |        |         |
2347  AAGCAGGCAATGCAGTCCGGTAGTGGTCCAAGCTGGACCCTCGATGGTGAGTTTGATTTTGAAGACGAC    2415
      Lys Gln Ala METGln Ser Gly Ser Gly Pro Ser Trp Thr Leu Asp Gly Glu Phe Asp Phe Glu Asp Asp
                 2364       2372      2379        2388
                 2364                 2382

HaeIII                                                   SacI
                 ApaI          HaeIII                                    AluI
                  | |             |                                       | |
2416  GTGGAGAACCAACAACAGGGCCCGCAGCAGAGGCCACCGCTGCTCCAGCAGTGCTGCAACGAGCTCCAC    2484
      Val Glu Asn Gln Gln Gln Gly Pro Gln Gln Arg Pro Pro Leu Leu Gln Gln Cys Cys Asn Glu Leu His
                         2438         2449                                  2479
                         2436                                               2481

TaqI
       BstNI                                                        HinfI
         |                                                            | |
2485  CAGGAAGAGCCACTTTGCGTTTGCCCAACCTTGAAAGGAGCATCCAAAGCCGTTAAACAACAGATTCGA    2553
      Gln Glu Glu Pro Leu Cys Val Cys Pro Thr Leu Lys Gly Ala Ser Lys Ala Val Lys Gln Ile Arg
        2486                                                        2548
                                                                    2551

2554  CAACAACAGGGACAACAAATGCAGGGACAGCAGATGCAGCAAGTGATTAGCCGTATCTACCAGACCGCT    2622
      Gln Gln Gln Gly Gln Gln METGln Gly Gln Gln METGln Gln Val Ile Ser Arg Ile Tyr Gln Thr Ala

AluI                                                            BstNI
                 |                                                                |
2623  ACGCACTTACCTAGAGCTTGCAACATCAGGCAAGTTAGCATTTGCCCCTTCCAGAAGACCATGCCTGGG    2691
      Thr His Leu Pro Arg Ala Cys Asn Ile Arg Gln Val Ser Ile Cys Pro Phe Gln Lys Thr METPro Gly
              2639                                                              2688
```

-continued
Lambda CGN1-2
NCG-186 Linear
LENGTH = 4325

```
              MapI
              HpaII
              HaeIII                          XhoI
              ApaI         HinfI              TaqI            AccI
              │││          │                  ││              │
2692  CCCGGCTTCTACTAGATTCCAAACGAATATCCTCGAGAGTGTGTATACCACGGTGATATGAGTGTGGTT  2760
      Pro Gly Phe Tyr
              2694         2707               2724            2736
              2692                            2725
              2694                            2724
              2694

HincII                                        RsaI
              │                                             │
2761  GTTGATGTATGTTAACACTACATAGTCATGGTGTGTGTTCCATAAATAATGTACTAATGTAATAAGAAC  2829
              2771                                          2813

AccI
         │
2830  TACTCCGTAGACGGTAATAAAAGAGAAGTTTTTTTTTTTACTCTTGCTACTTTCCTATAAAGTGATGAT  2898
         2838

ScaI
                                                          RsaI
                                                          │
2899  TAACAACAGATACACCAAAAAGAAAACAATTAATCTATATTCACAATGAAGCAGTACTAGTCTATTGAA  2967
                                                          2954
                                                          2954

Sau3AI
                                                                       │
2968  CATGTCAGATTTTCTTTTTCTAAATGTCTAATTAAGCCTTCAAGGCTAGTGATGATAAAGATCATCCA  3036
                                                                         3028

Sau3AI                   Sau3AI
         BamHI        HinfI       BclI
         │            │           │
3037  ATGGGATCCAACAAAGACTCAAATCTGGTTTTGATCAGATACTTCAAAACTATTTTTGTATTCATTAAA  3105
         3041         3053        3069
         3041                     3069

HinfI
                      │
3106  TTATGCAAGTGTTCTTTTATTTGGTGAAGACTCTTTAGAAGCAAAGAACGACAAGCAGTAATAAAAAAA  3174
                      3135

3175  ACAAAGTTCAGTTTTAAGATTTGTTATTGACTTATTGTCATTTGAAAAATATAGTATGATATTAATATA  3243

3244  GTTTTATTTATATAATGCTTGTCTATTCAAGATTTGAGAACATTAATATGATACTGTCCACATATCCAA  3312

NdeI
                                 │
3313  TATATTAAGTTTCATTTCTGTTCAAACATATGATAAGATGGTCAAATGATTATGAGTTTTGTTATTTAC  3381
                                 3341

TaqI
              AluI                         RsaI    Sau3AI
              │ │                          │       │
3382  CTGAAGAAAAGATAAGTGAGCTTCGAGTTTCTGAAGGGTACGTGATCTTCATTTCTTGGCTAAAAGCGA  3450
              3402                         3421
              3405                                 3425

3451  ATATGACATCACCTAGAGAAAGCCGATAATAGTAAACTCTGTTCTTGGTTTTTGGTTTAATCAAACCGA  3519

MspI                                                       MspI
         HpaII DdeI                                           HinfI HpaII
         │    AluI                        NdeI                │     │
3520  ACCGGTAGCTGAGTGTCAAGTCAGCAAACATCGCAAACCATATGTCAATTCGTTAGATTCCCGGTTTAA  3588
         3522 3528                        3560                3576  3581
         3522 3529                                                  3581
```

-continued

Lambda CGN1-2

NCG-186 Linear

LENGTH = 4325

```
             MspI
             HpaII
              |
3589  GTTGTAAACCGGTATTTCATTTGGTGAAAACCCTAGAAGCCAGCCANCCTTTTTAATCTAATTTTTGCA  3657
             3598
             3598

HinfI
                                                             HincII
                                            DdeI             | |    BstNI
                                             |               | |     |
3658  AACGAGAAGTCACCACACCTCTCCACTAAAACCCTGAACCTTAGTGAGAGAAGCAGAGNCANNAAAGAA  3726
                                            3702              3718
                                                            3715
                                                            3714

3727  CAAATAAAACCCGAAGATGAGACCACCACGTGCGGCGGGACGTTCAGGGGACGGGGAGGAAGAGAATGR  3795

AvaII
           |  AluI                                                           AvaII
           |   |                                                               |
3796  CGGCGG5MNTTTGGTGGCGGCGGCGGACGTTTTGGTGGCGGCGGTGGACGTTTTGGTGGCGGCGGTGGA  3864
           3804                                                              3863
          3801

EcoRV        AvaII                                   DdeI
                     |            |                                       |
3865  CCTTTGGTGGTGGATATCGTGACGAAGGACCTCCCAGTGAAGTCATTGGTTCGTTTACTCTTTTCTTAG  3933
                    3880         3892                                    3930

TaqI                                  HindIII
       HinfI                                  AluI                          DdeI
       | |                                    | |                            |
3934  TCGAATCTTATTCTTGCTCTGCTCGTTGTTTTACCGATAAAGCTTAAGACTTTATTGATAAAGTTCTCA  4002
         3937                                 3976                         4000
        3935                                 3974

AluI      XmnI                                       HinfI     DdeI
        |         |                                           |        |
4003  GCTTTGAATGTGAATGAACTGTTTCCTGCTTATTAGTGTTCCTTTGTTTTGAGTTGAATCACTGTCTTA  4071
       4004      4023                                        4059     4069

HinfI
               |
4072  GCACTTTTGTTAGATTCATCTTTGTGTTTAAGTTAAAAGGTAGAAACTTTGTGACTTGTCTCCGTTATG  4140
              4085

HincII
          |
4141  ACAAGGTTAACTTTGTTGGTTATAACAGAAGTTGCGACCTTTCTCCATGCTTGTGAGGGTGATGCTGTG  4209
         4146

AvaII  AluI DdeI  Sau3AI
       |     |    |     |
4210  GACCAAGCTCTCTCAGGCGAAGATCCCTTACTTCAATGCCCCAATCTACTTGGAAAACAAGACACAGAT  4278
      4210   4217 4222  4231
```

-continued
Lambda CGN1-2
NCG-186 Linear
LENGTH = 4325

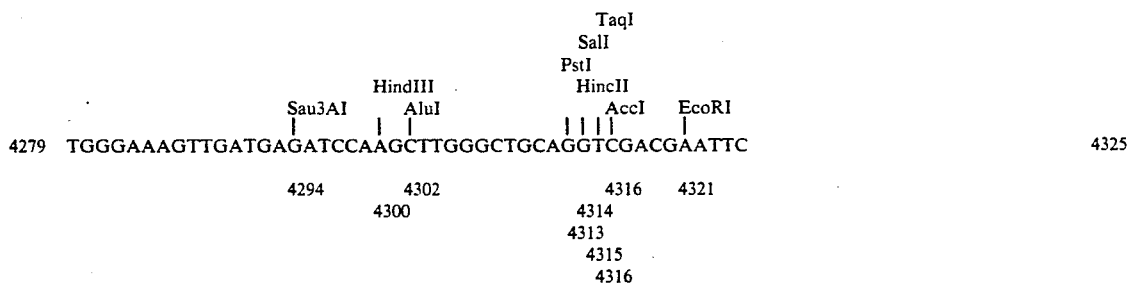

The lambda CGN1-2 napin gene is that encoding the mRNA corresponding to the BE5 cDNA as determined by the exact match of their nucleotide sequences.

An expression cassette was constructed from the 5'-end and 3'-end of the lambda CGN1-2 napin gene as follows in an analogous manner to the construction of pCGN944. The majority of the napin coding region of pCGN940 was deleted by digestion with SalI and religation to form pCGN1800. Single-stranded DNA from pCGN1800 was used in an in vitro mutagenesis reaction (Adelman et al., DNA (1983) 2:183–193) using the synthetic oligonucleotide 5'-GCTTGTTCGCCATG-GATACTTGTGTATGTTC-3'. This oligonucleotide inserted on EcoRV and an NcoI restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with synthetic linker described above in place of the normal polylinker) cut from EcoRI and blunted by filling in with DNA Polymerase I Klenow fragment to create pCGN1802. 3' sequences from the lambda CGN1-2 napin gene were added to XhoI/HindIII digested pCGN1802 to complete the cassette by ligation to pCGN941 digested with XhoI and HindIII. The resulting expression cassette, pCGN1803 contains 1.725 kb of napin promoter sequence, and 1.265 kb of napin 3' sequences with the unique cloning sites SalI, BglII, PstI and XhoI in between.

The ACP-precursor coding region from pCGN1Bcs is excised by double digestion with XhoI and EcoRI and ligated to the cloning vector pUC18 previously digested with SalI and EcoRI. Transformation of ligated DNA into the appropriate E. coli host and screening using the penicillin-resistant, blue-white screening system of pUC vectors (Vieira and Messing, Gene (1982) 19:259–268) generates a plasmid containing a unique Dra3 site located downstream of the stop codon for the ACP-precursor coding region. Digestion with Dra3 followed by ligation with a PstI linker generates a plasmid in which the coding region is cleanly excised as a BglII to PstI fragment, which is cloned into PstI and BglII sites of pCGN1803 with the proper orientation of the ACP-precursor coding region to the napin promoter and terminator parts of the embryo-specific expression information encoded by pCGN1803. The resulting chimeric gene is then introduced into a binary vector and transferred to Agrobacterium for cocultivation with Brassica napus hypocotyl segments employing the same conditions employed for the spinach ACP chimeric gene in pCGN946.

In accordance with the subject invention, sequences coding for functional acyl carrier protein, particularly plant acyl carrier protein, are provided, which can be used as probes for detecting the presence of acyl carrier protein genes, for screening libraries from plants and bacteria, either genomic or cDNA, for use in assays for detecting the presence of acyl carrier protein genes, and the like. In addition, the coding sequence can be used in the preparation of expression constructs, where the coding sequence is combined with transcriptional and translational initiation and termination regulatory regions for expression in an appropriate host in which the regulatory regions are functional. Of particular interest is the use of the ACP coding sequence in conjunction with a transcription initiation region which is functional in a plant and particularly is regulated so as to provide for expression in seed. In this manner, the production of seed oil can be enhanced and, as appropriate, the fatty acid composition modulated.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A cDNA sequence coding for plant acyl carrier protein wherein said cDNA sequence is obtainable from spinach or Brassica.

2. A cDNA sequence coding for a spinach acyl carrier protein.

3. A cDNA sequence coding for a Brassica acyl carrier protein.

4. A cDNA sequence according to claim 3, wherein said Brassica is *campestris*.

5. A cDNA sequence according to claim 3, wherein said Brassica is *napus*.

6. A DNA construct comprising a sequence coding for a plant acyl carrier protein obtainable from spinach or Brassica and a sequence other than at least one of the transcriptional or translational initiation or termination regions naturally associated with said sequence coding for a plant acyl carrier protein.

7. A DNA construct according to claim 6 wherein said construct further comprises in the 5'-3' direction of transcription, a transcriptional initiation region and a translational initiation region functional in a cellular host, and wherein said sequence coding for a plant acyl carrier protein is an open reading frame coding for a plant acyl carrier protein obtainable from spinach or Brassica, and translational and transcriptional termination regions functional in said host, wherein expression of said open reading frame is regulated by said initiation and termination regions and wherein at least one of said initiation and termination regions is other than the initiation and termination region naturally occurring with said open reading frame.

8. A DNA construct according to claim 7, wherein said open reading frame encodes for spinach or Brassica acyl carrier protein.

9. A DNA construct according to claim 7, wherein said initiation and termination regions are functional in a plant host.

10. A DNA construct according to claim 9, wherein said transcriptional initiation region provides for transcription in seed.

11. A DNA construct according to claim 9, wherein said transcriptional initiation region provides for transcription in a developing embryo.

12. A DNA construct according to claim 11, wherein said transcriptional initiation region is a napin regulatory region.

13. A Ti- or Ri-plasmid comprising a DNA construct according to any one of claims 7-12.

14. A plant cell comprising a DNA construct according to any one of claims 7-12.

15. A plant cell according to claim 14, wherein said plant cell is an embryonic cell and part of a seed.

16. A plant cell according to claim 15, wherein said plant is a Brassica plant.

17. A method for producing a peptide product in a plant cell by recombinant techniques, where a plant cell is transformed with an expression cassette to provide a transgenic cell comprising a gene encoding said peptide product and said transgenic cell is grown whereby said gene is expressed and said peptide product is produced, the improvement which comprises:
obtaining said peptide product in a chloroplast or leucoplast by employing as said gene an open reading frame encoding a spinach or Brassica acyl carrier protein, said open reading frame encoding said peptide product and an amino acid sequence capable of functioning as a transit peptide, whereby said peptide product is produced as a precursor peptide and is translocated to said chloroplast or leucoplast.

18. A method according to claim 17, wherein said plant is a Brassica plant.

19. A method according to claim 18, wherein said expression cassette comprises a napin transcriptional initiation regulatory region.

20. A cDNA sequence coding for a precursor plant acyl carrier protein, wherein said cDNA sequence is obtainable from spinach or Brassica.

21. A cDNA sequence comprising:
an open reading frame coding for a plant acyl carrier protein, wherein said cDNA sequence is obtainable from spinach or Brassica.

22. The cDNA sequence according to claim 21, wherein said open reading frame includes a transit peptide sequence capable of providing for intracellular translocation of said acyl carrier protein.

23. The cDNA sequence according to claim 22, wherein said intracellular translocation is to a leucoplast or a chloroplast.

24. A DNA sequence comprising:
a first DNA sequence encoding a plant acyl carrier protein, wherein said DNA sequence is obtainable from spinach or Brassica, joined in vitro to a second DNA sequence encoding a transit peptide sequence obtainable from spinach or Brassica and capable of providing for intracellular translocation of said acyl carrier protein.

25. A DNA sequence encoding an amino acid sequence obtainable from spinach or Brassica and capable of providing for translocation of a polypeptide of interest to a leucoplast or a chloroplast, wherein said amino acid sequence is encoded by a cDNA sequence coding for a spinach or Brassica acyl carrier protein.

26. A DNA sequence obtainable from spinach or Brassica encoding an amino acid sequence capable of providing for intracellular translocation of a polypeptide of interest, said amino acid sequence being identified by the process of:
analyzing the nucleotide sequence of a cDNA clone which hybridizes to an acyl carrier protein gene probe.

27. A cDNA sequence encoded by pCGN1SOL, wherein said sequence encodes a transit peptide comprising 56 amino acids.

28. The method according to claim 17, wherein said transit peptide is other than the native transit peptide associated with said precursor peptide.

29. A cDNA sequence according to claim 1 wherein said cDNA sequence is a spinach or ACP-I sequence.

* * * * *